US011873475B2

United States Patent
Chapnick et al.

(10) Patent No.: US 11,873,475 B2
(45) Date of Patent: Jan. 16, 2024

(54) SYSTEMS AND METHODS FOR CELL SORTING AND CELL EXTRACTION

(71) Applicant: BIOLOOMICS, INC., Boulder, CO (US)

(72) Inventors: Douglas Chapnick, Boulder, CO (US); Jeremy Jacobsen, Broomfield, CO (US)

(73) Assignee: BIOLOOMICS, INC., Boulder, CO (US)

( * ) Notice: Subject to any disclaimer, the term of this patent is extended or adjusted under 35 U.S.C. 154(b) by 0 days.

(21) Appl. No.: 17/790,705

(22) PCT Filed: Dec. 23, 2020

(86) PCT No.: PCT/US2020/066930
§ 371 (c)(1),
(2) Date: Jul. 1, 2022

(87) PCT Pub. No.: WO2021/138212
PCT Pub. Date: Jul. 8, 2021

(65) Prior Publication Data
US 2023/0002719 A1    Jan. 5, 2023

Related U.S. Application Data

(60) Provisional application No. 62/956,842, filed on Jan. 3, 2020.

(51) Int. Cl.
*G06K 9/00* (2022.01)
*C12M 1/00* (2006.01)
(Continued)

(52) U.S. Cl.
CPC ......... *C12M 47/04* (2013.01); *G01N 15/1463* (2013.01); *G01N 35/00584* (2013.01);
(Continued)

(58) Field of Classification Search
None
See application file for complete search history.

(56) References Cited

U.S. PATENT DOCUMENTS 4,729,949 A    3/1988   Weinreb et al.
9,593,808 B1 *  3/2017   Gaitas ............. G01N 33/54366
(Continued)

FOREIGN PATENT DOCUMENTS

WO    WO 2016193200 A1    12/2016
WO    WO 2019204333 A1    10/2019
WO    WO-2019204333 A1 *  10/2019    ............. G01N 15/10

OTHER PUBLICATIONS

Cai, Shaobo, et al. "Novel 3D electrospun scaffolds with fibers oriented randomly and evenly in three dimensions to closely mimic the unique architectures of extracellular matrices in soft tissues: fabrication and mechanism study." Langmuir 29.7 (2013): 2311-2318. (Year: 2013).*

(Continued)

*Primary Examiner* — Avinash Yentrapati
(74) *Attorney, Agent, or Firm* — COZEN O'CONNOR

(57) ABSTRACT

A cell sorter includes a base for holding a cell culture plate containing a fluorescently labeled sample of cells, a fluorescence imager for viewing the cell culture plate, through bottom of the cell culture plate, to capture one or more fluorescence images of the fluorescently labeled sample of cells, and a cell extraction module for extracting a cell selected based on the one or more fluorescence images. The cell extraction module includes a needle for hydraulically removing the selected cell from the cell culture plate, and a motorized translation stage for translating the needle in a z-dimension to reach the selected cell from above. The cell sorter further includes a motorized translation stage for translating one of the needle and the cell culture plate in x-

(Continued)

and y-dimensions, relative to the other one of the needle and the cell culture plate, to position the needle over selected first cell.

13 Claims, 4 Drawing Sheets

(51) Int. Cl.
    *G01N 15/14*     (2006.01)
    *G01N 35/00*     (2006.01)
    *G01N 15/10*     (2006.01)

(52) U.S. Cl.
    CPC ............... *G01N 2015/1006* (2013.01); *G01N 2015/149* (2013.01)

(56) References Cited

U.S. PATENT DOCUMENTS

| | | | |
|---|---|---|---|
| 2006/0073076 A1* | 4/2006 | Ichiki | G01N 15/1484 422/81 |
| 2013/0027539 A1* | 1/2013 | Kiyota | C12M 41/36 348/79 |
| 2013/0065795 A1* | 3/2013 | Allbritton | C12M 25/04 506/40 |
| 2013/0190212 A1* | 7/2013 | Handique | G01N 1/28 506/40 |
| 2016/0367233 A1* | 12/2016 | Mamiya | A61B 1/05 |
| 2017/0273712 A1* | 9/2017 | Carlson | A61B 10/04 |
| 2018/0224473 A1* | 8/2018 | Reed | G01N 35/0092 |
| 2019/0321013 A1* | 10/2019 | Nieminen | A61B 10/0233 |
| 2019/0359929 A1* | 11/2019 | Kishii | C12M 25/00 |
| 2020/0261170 A1* | 8/2020 | Ziso | A61B 34/30 |

OTHER PUBLICATIONS

PCT/US2020/066930 International Search Report and Written Opinion dated May 12, 2021; 17 pages.

European Patent Application No. 20909136.2, Search and Opinion dated Feb. 20, 2023, 7 pages.

* cited by examiner

SYSTEMS AND METHODS FOR CELL SORTING AND CELL EXTRACTION

CROSS-REFERENCE TO RELATED APPLICATION

This application claims priority to U.S. Provisional Patent Application No. 62/956,842, filed Jan. 3, 2020, the entire content of which is incorporated herein.by reference.

SUMMARY

In an embodiment, a cell sorter includes (a) a base configured to hold a cell culture plate containing a fluorescently labeled sample of cells, (b) a fluorescence imager configured to view the cell culture plate, through bottom of the cell culture plate, to capture one or more fluorescence images of the fluorescently labeled sample of cells, and (c) a cell extraction module configured to extract, from above the cell culture plate, a first cell selected from the sample of cells based on the one or more fluorescence images. The cell extraction module includes a needle configured to hydraulically remove the first cell from the cell culture plate, and a first motorized translation stage for translating the needle in a z-dimension to reach the first cell from above. The cell sorter further includes a second motorized translation stage for translating one of the needle and the cell culture plate in x- and y-dimensions, relative to the other one of the needle and the cell culture plate, to position the needle over the first cell.

In an embodiment, a cell sorting method includes (a) capturing, through a bottom of a cell culture plate, one or more fluorescence images of a fluorescently labeled sample of cells disposed in the cell culture plate, (b) based upon the one or more fluorescence images, selecting a first cell from the sample of cells and recording location of the first cell in the cell culture plate, and (c) extracting the first cell from the cell culture plate. The step of extracting includes positioning a needle above the location, lowering the needle to the first cell, and hydraulically removing the first cell with the needle.

In an embodiment, a cell extraction module for extracting a pre-selected cell from a sample of cells in a cell culture plate includes (a) a needle configured to hydraulically remove the pre-selected cell from the cell culture plate, (b) a motorized translation stage mechanically coupled with the needle and configured to translate the needle, in a dimension orthogonal to the cell culture plate, to reach the pre-selected cell from above, and (c) a sensor, coupled to the needle, and configured to be communicatively coupled to the motorized translation stage to stop downward translation of the needle, by the motorized translation stage, when the needle, according to the sensor, is (i) in a threshold degree of contact with at least one of the pre-selected cell and the cell culture plate or (ii) at a threshold distance above at least one of the pre-selected cell and the cell culture plate.

In an embodiment, a method for extracting a pre-selected cell from a sample of cells in a cell culture plate includes (a) recording location of the pre-selected cell in an x-y plane of the cell culture plate, the location being the location of the pre-selected cell while the cells are adhered to the cell culture plate, (b) chemically or biochemically reducing adherence of the sample of cells to the cell culture plate without changing position of the cells in the cell culture plate, and (c) positioning a needle at a first position that is aligned to the location in the x-y plane while being a non-zero distance above the location in a z-dimension orthogonal to the x-y plan. The method further includes, after the steps of reducing adherence and positioning the needle, (d) lowering the needle, in the z-dimension, to the pre-selected cell, and (e) hydraulically removing the pre-selected cell with the needle.

DESCRIPTION OF EXAMPLE EMBODIMENTS

Figure 1:
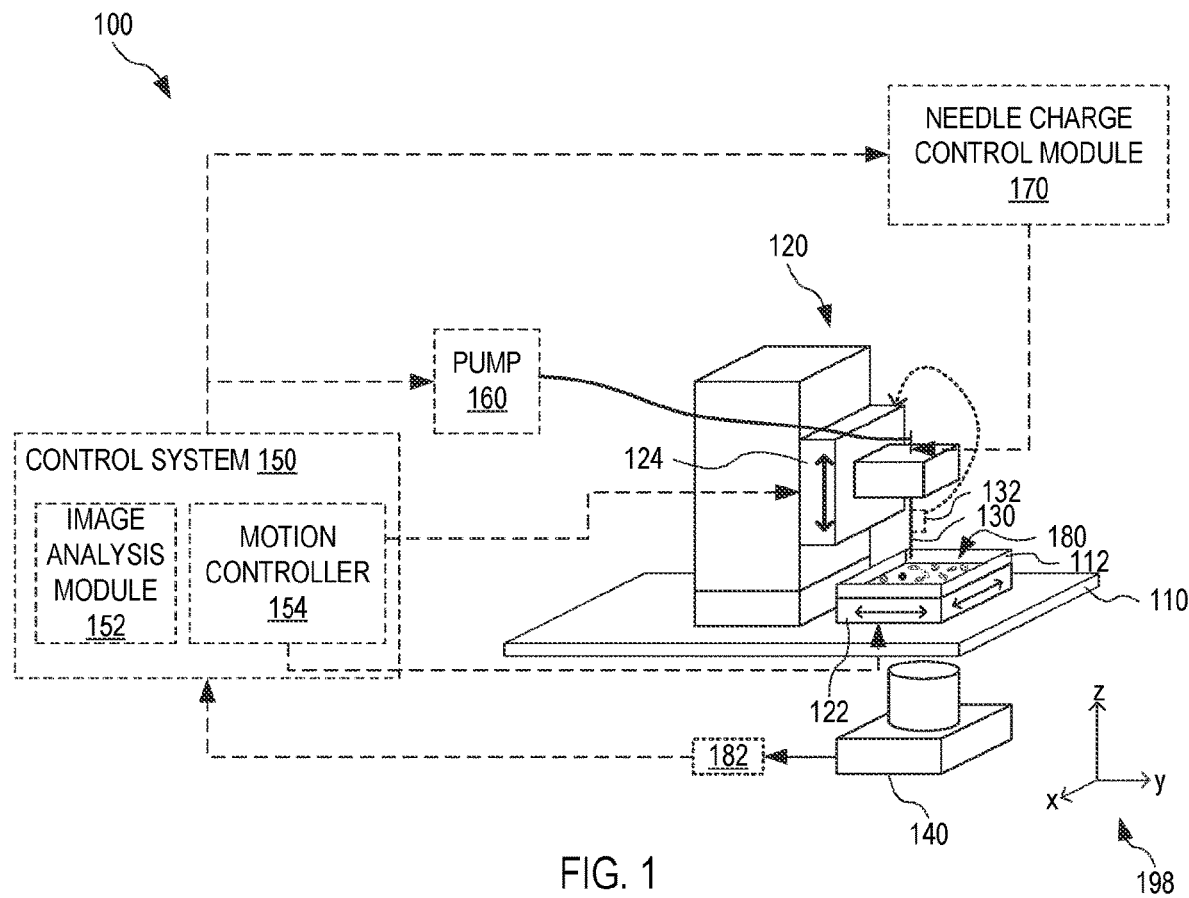
FIG. 1 illustrates a cell sorter, according to an embodiment.

FIG. 1 illustrates one cell sorter 100 for automatic extraction and sorting of cells based on fluorescence imaging of the cells. Cell sorter 100 includes a base 110, a fluorescence imager 140, and a cell extraction module 120. In operation, a cell culture plate 112, containing a fluorescently labeled sample 180 of cells, is placed on base 110. Fluorescence imager 140 views cell culture plate 112 from underneath to capture one or more fluorescence images 182 of sample 180 through the bottom of cell culture plate 112. Cell extraction module 120 extracts, from above cell culture plate 112, a cell selected from sample 180 based on fluorescence image(s) 182.

Cell culture plate 112 may be (a) a single-well cell culture plate for parallel evaluation of a plurality of cells in the same sample, or (b) a multiwell culture plate for parallel processing of a plurality of separate samples. When cell culture plate 112 is a multiwell culture plate, each well may contain a plurality of cells that are evaluated in parallel. The cells in sample 180 may be mammalian, yeast, or bacterial cells in culture.

In one scenario, cell sorter 100 processes a set of separate cell samples, each of which has been exposed to a different drug, and cell sorter 100 extracts cells that respond to the drugs in a certain fashion. Each sample may contain a plurality of cells that having a respective plurality of different genetic encodings that potentially affect the response of the cells to the drugs. In this scenario, many different cell samples may be processed in parallel in a single multiwell culture plate, in a series of single-well culture plates, or in a series of multiwell culture plates. The extracted cells may be cultured separately and used as biosensors in a drug discovery process or in a synthetic biosensor gene discovery process.

Figure 2:
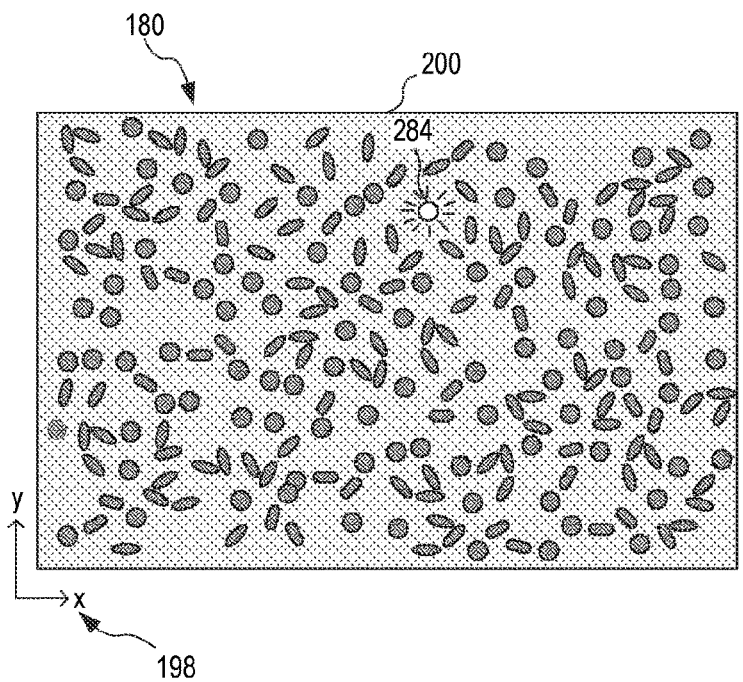
FIG. 2 illustrates an example fluorescence image of a sample of cells.

FIG. 2 illustrates one fluorescence image 200 of sample 180. Fluorescence image 200 is an example of fluorescence image 182 and is taken in the x-y plane of a coordinate system 198. In this example, a cell 284 is selected for extraction by cell extraction module 120 based on the appearance of cell 284 in fluorescence image 200. Cell 284 may be selected according to its fluorescence properties in fluorescence image 200, and/or its morphology as it appears in fluorescence image 200.

Throughout this disclosure, reference to x, y, and z dimensions refers to the x, y, and z dimensions, respectively, of coordinate system 198.

Referring again to FIG. 1, cell extraction module 120 includes a needle 130 and motorized translation stages 122 and 124. Translation stage 122 is a two-dimensional translation stage configured to translate cell culture plate 112 in the x and y dimensions so as to position needle 130 over the selected cell (e.g., cell 284). Translation stage 122 may be incorporated in base 110, for example as part of a microscope that includes fluorescence imager 140. In an alternative embodiment, not shown in FIG. 1, translation stage 122 is instead configured to translate needle 130 in the x and y dimensions. Translation stage 124 is a one-dimensional translation stage configured to translate needle 130 in the z dimension to reach the selected cell from above.

In certain embodiments, cell sorter 100 further includes a control system 150 automatically controls needle 130, according to fluorescence image(s) 182, to extract the selected cell. Control system 150 may include an image analysis module 152 that analyzes fluorescence image(s) 182 to automatically select a cell for extraction and record its location in the x-y plane. Image analysis module 152 may apply a computational algorithm to fluorescence image(s) 182 to identify a cell that meets one or more criteria for selection. Image analysis module 152 may be configured to select a cell according to an analysis of intensity of two fluorescence color channels. The two fluorescence color channels may be two color channels of FRET (Forster resonance energy transfer) fluorescence.

Control system 150 may also include a motion controller 154 that controls translation stages 122 and 124 to position needle 130 at the selected cell. Motion controller 154 controls translation stage 122 to adjust the position of needle 130 in the x-y plane to position needle 130 at the recorded location of the selected cell in the x-y plane. After that needle 130 has been placed at the recorded location in the x-y plane, motion controller 154 controls translation stage 124 to lower needle 130 to the selected cell such that needle 130 can remove the selected cell from cell culture plate 112. Motion controller 154 may then control translation stages 122 and 124 to deposit the extracted cell elsewhere, such as in a suitable container. In one implementation, control system 150 includes a processor and a non-transitory memory encoding machine-readable instructions that, when executed by the processor, controls the processor to (a) perform the control functions of control system 150 and/or (b) effect that the control functions of control system 150 be performed by other electronic circuitry.

Cell sorter 100 may further include a pump 160 that is hydraulically coupled to needle 130. Pump 160 is, for example, a peristaltic pump or a piston pump. The piston pump may include a gas-tight sterile syringe. Control system 150 may be configured to control pump 160 to remove the selected cell when needle 130 is placed at the selected cell.

In one embodiment, fluorescence imager 140 includes an image sensor and an imaging objective. The image sensor may be a CCD image sensor or a CMOS image sensor. In this embodiment, the imaging objective images fluorescence from sample 180 onto the image sensor, such that the image sensor can capture the fluorescence image. The image sensor may be a color image sensor such that the image sensor may capture several different spectral types of fluorescence in one shot. Alternatively, the image sensor may be a monochrome image sensor. Even in the case of a monochrome image sensor, fluorescence imager 140 may be operated to discriminately image different spectral types of fluorescence. For example, fluorescence imager 140 may include two or more fluorescence emission filters that are inserted into the optical train of fluorescence imager 140 one at a time, to capture a different fluorescence image for each of the two or more fluorescence emission filters. Selection of a cell for extraction may be based on a comparison of two or more resulting fluorescence images.

In another embodiment, fluorescence imager 140 is a scanning system that includes a photomultiplier tube (or another photodetector) and a motorized translation stage configured to scan position of the photomultiplier tube relative to cell culture plate 112, to build the one or more fluorescence images by scanning. Also in this embodiment, fluorescence imager 140 may include two or more fluorescence emission filters that are inserted into the optical train of fluorescence imager 140 one at a time, to capture a different fluorescence image for each of the two or more fluorescence emission filters.

Although shown in FIG. 1 as being located beneath base 110, a portion of fluorescence imager 140, such as an image sensor or photomultiplier tube, may be located elsewhere and utilize relay optics to view cell culture plate 112 from underneath, so as to image sample 180 through a bottom of cell culture plate 112.

Figure 3:
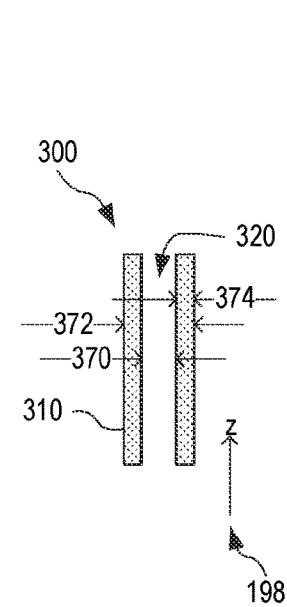
FIG. 3 is a cross-sectional view of a needle end, according to an embodiment.

FIG. 3 is a cross-sectional view of a needle end 300, with the cross section being orthogonal to the x-y plane. Needle end 300 is an embodiment of the end of needle 130 closest to cell culture plate 112. Needle end 300 is tube-shaped and has a wall 310 that forms a channel 320 into which a selected cell may be collected. Needle end 300 has an inner diameter 370 and an outer diameter 372. Wall 310 has a thickness 374. Without departing from the scope hereof, two or more of inner diameter 370, outer diameter 372, and thickness 374 may vary in the z-dimension. In order to remove a selected cell without also removing other nearby non-selected cells, the dimensions of needle end 300 are generally small. In one embodiment, inner diameter 370 is in the range between 5 and 200 microns. Thickness 374 is, for example, 100 microns or less. In one example, inner diameter 370 is between 25 and 50 microns (e.g., 35 microns), and outer diameter 372 is between 100 and 150 microns (e.g., 120 microns). Needle end 300 may be made of a metal, such as stainless steel. With the small dimensions mentioned here, needle end 300 may be relatively fragile and likely to be damaged if driven into the bottom of cell culture plate 112 with a certain force.

Referring again to FIG. 1, cell extraction module 120 may incorporate a mechanism that positions needle 130 within sufficient proximity of a cell selected for extraction while protecting needle 130 from pressing against cell culture plate 112 with sufficient force to damage the end of needle 130. In one such embodiment, cell extraction module 120 includes a sensor 132 coupled to needle 130. Sensor 132 is communicatively coupled to translation stage 124 to stop downward translation of needle 130, by translation stage 124, when needle 130, according to sensor 132, is (a) in a threshold degree of contact with cell culture plate 112 and/or the selected cell or (b) at a threshold distance above cell culture plate 112 and/or the selected cell. Sensor 132 may be communicatively coupled with translation stage 124 via control system 150, such that control system 150 either allows or prevents downward translation by translation stage 124 according to an output or state of sensor 132.

In one implementation, sensor 132 includes a pressure sensor that senses when needle 130 reaches the bottom of cell culture plate 112. In another implementation, sensor 132 includes an electrical sensor that senses when needle 130 is in electrical contact with cell culture plate 112 and/or sample 180. In this implementation, sensor 132 may detect, electrically, that needle 130 has reached sample 180 and thus stop translation stage 124 from lowering needle 130 all the way to the bottom of cell culture plate 112. Needle 130 may be mounted in cell extraction module 120 in a manner that allows needle 130 to slide upwards when pushed by a threshold force, such that, even if translation stage 124 continues downward translation of needle 130 slightly beyond contact with the bottom of cell culture plate 112, needle 130 is protected from pressing on cell culture plate 112 with high pressure.

In another implementation, sensor 132 includes at least one of a photodetector and a light source. In embodiments, sensor 132 is, or includes, one of an optical proximity sensor and an optical limit switch. In embodiments, sensor 132 is an acoustic sensor, such as an ultrasonic proximity sensor.

In an example use scenario, cell extraction module 120 uses sensor 132 to position needle 130 no more than 1-2 microns above the cell selected for extraction, while the manufacturing tolerance for flatness of the bottom of cell culture plate 112, in this scenario, is at least 100 microns. For example, in the case of a multiwell plate, different wells may have depth that differ from each other by up to approximately 100 microns or even greater. In such situations, sensor 132 facilitates accurate and rapid positioning of needle 130, in each of a series of wells, within sufficient proximity of the cell selected for extraction while protecting needle 130 from damaging impact on the bottom of the wells.

When needle 130 is in contact with sample 180, needle 130 may pick up debris from sample 180. It may be beneficial to clean this debris off needle 130 before using needle 130 again to remove another cell. Cellular debris is predominantly negatively charged plasma membrane. In an embodiment, cell sorter 100 is configured to apply a transient negative electrical charge to needle 130 to assist with cleaning of needle 130. In this embodiment, cell sorter 100 may include a needle charge control module 170 that applies a transient, negative electrical charge to needle 130 when needle 130 is lowered into a liquid medium. This transient, negative electrical charge serves to repel, from needle 130 and into the liquid medium, negatively charged cellular debris. In operation, this cleaning may be performed in a dedicated cleaning fluid, or in sample 180. For example, needle charge control module 170 may apply the transient negative charge when needle 130 first contacts a liquid medium of sample 180 during downward translation of needle 130 toward a selected cell. Control system 150 may control needle charge control module 170.

Figure 4:
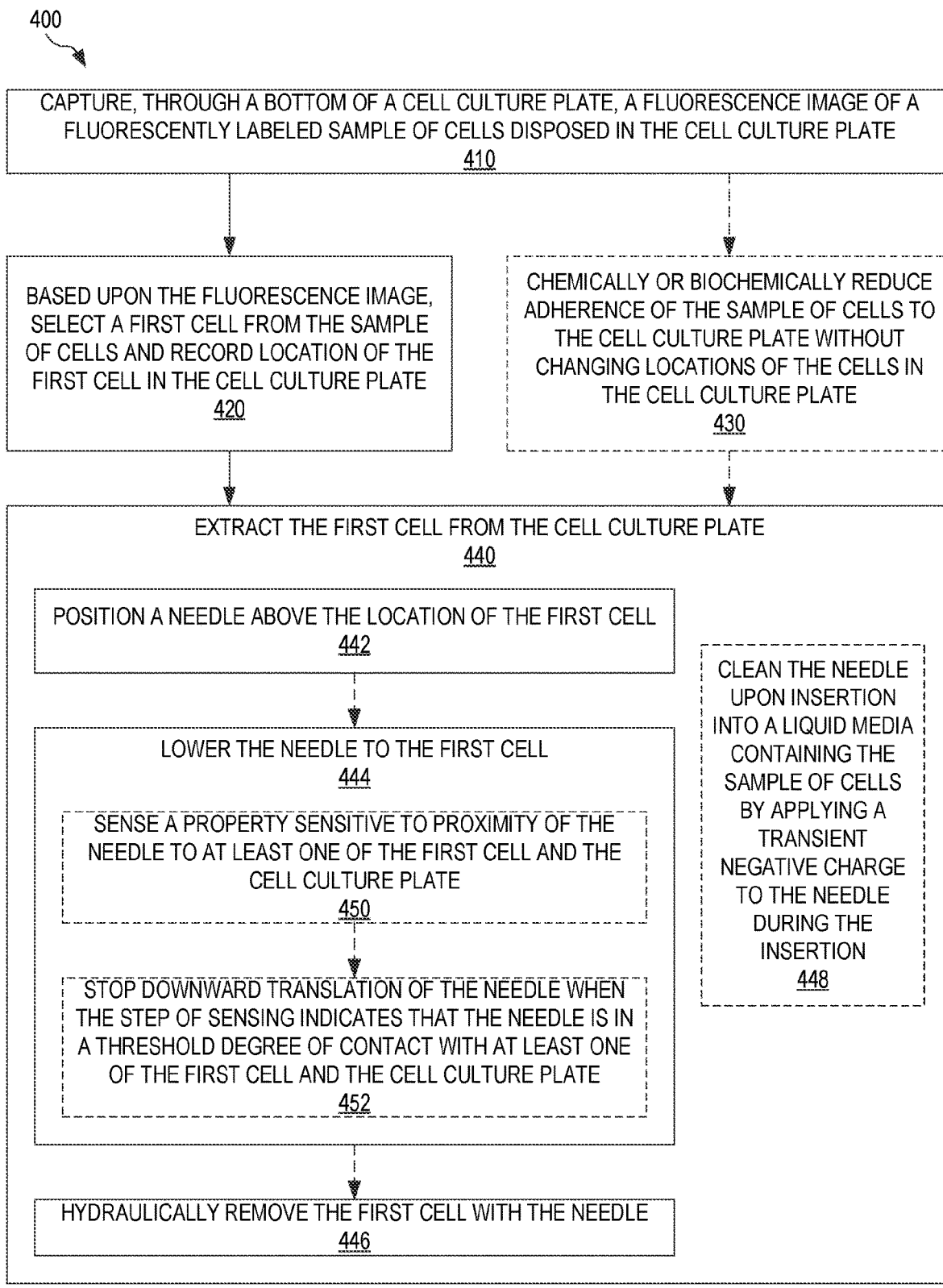
FIG. 4 illustrates a cell sorting method, according to an embodiment.

FIG. 4 illustrates one cell sorting method 400 that may be performed by cell sorter 100. Method 400 includes steps 410, 420, and 440. Step 410 captures, through a bottom of a cell culture plate, one or more fluorescence images of a fluorescently labeled sample of cells disposed in the cell culture plate. In one example of step 410, fluorescence imager 140 captures one or more fluorescence images 182 of sample 180 through the bottom of cell culture plate 112. Step 420 selects, based upon the one or more fluorescence images captured in step 410, a cell from the sample of cells and records the location of the selected cell in the cell culture plate. In one example of step 420, image analysis module 152 processes fluorescence image(s) 182 to select a cell and record its location in the x-y plane.

Step 440 extracts the selected cell from the cell culture plate. Step 440 includes steps 442, 444, and 446. Step 442 positions a needle above the location recorded in step 420. Step 444 lowers the needle to the selected cell. Step 446 hydraulically removes the selected cell with the needle. Step 440 may be performed by cell extraction module 120, for example as controlled by control system 150. In one example of step 442, control system 150 controls translation stage 122 to position cell culture plate 112 such that needle 130 is above the location of the selected cell. Needle 130 is thereby placed at the x-y location of the selected cell in cell culture plate 112, but a non-zero distance in the z-dimension above sample 180. In one example of step 444, control system 150 controls translation stage 124 to lower needle 130 to the selected cell. In one example of step 446, control system 150 controls pump 160 to hydraulically remove the selected cell with needle 130.

In certain embodiments, step 444 includes steps 450 and 452. Step 450 senses a property sensitive to proximity of the needle to at least one of the first cell and the cell culture plate. In one example of step 450, sensor 132 senses proximity of needle 130 to the selected cell and/or cell culture plate 112. Step 452 stops downward translation of the needle when the step 450 indicates that the needle is (a) in a threshold degree of contact with at least one of the first cell and the cell culture plate or (b) at a threshold distance above at least one of the first cell and the cell culture plate. In one example of step 452, motion controller 154 stops downward translation by translation stage 124 when an output or state of sensor 132 indicates that needle 130 is (a) in a threshold degree of contact with at least one of the first cell and the cell culture plate or (b) at a threshold distance above at least one of the first cell and the cell culture plate.

In one use scenario, the cells in sample 180 are adhered to the cell culture plate before and during image capture in step 410. When implemented in this scenario, method 400 may include a step 430, performed after step 410 and before step 440, of chemically or biochemically reducing the adherence of the cells to the cell culture plate without changing locations of the cells in the cell culture plate. When a de-adhering agent is added in step 430, cells may change from a flattened, adhered state to a round state that is either not or only slightly adhered to the cell culture plate. Step 430 enables hydraulic removal of the selected cell in step 446 with no need for harsh removal processes such as scraping or local application of de-adhering agents. It is therefore possible to use a thin (and thus relatively fragile) needle, such as needle 130 with needle end 300, which in turn makes it possible to accurately and selectively extract the selected cell even when the selected cell is in close proximity to other non-selected cells. In one embodiment, step 430 adds EGTA to the cell culture plate to reduce the adherence of cells to the cell culture plate. In another embodiment, step 430 utilizes another agent, for example selected from the group consisting of EDTA, trypsin, and nonspecific proteases. Cell sorter 100 does not require movement of cell culture plate 112 between fluorescence imaging in step 410 and cell extraction in step 440, and the cells therefore stay in place even though they are not adhered or only weakly adhered to cell culture plate 112.

In situations where step 420 identifies several cells that meet the selection criteria, method 400 may perform step 440 once for each such cell.

Step 440 may include a step 448 of clean the needle upon insertion into a liquid media containing the sample of cells by applying a transient negative charge to the needle during the insertion. In one example of step 448, needle charge control module 170 applies a transient, negative electrical charge to needle 130 while needle 130 is being inserted in sample 180.

Figure 5:
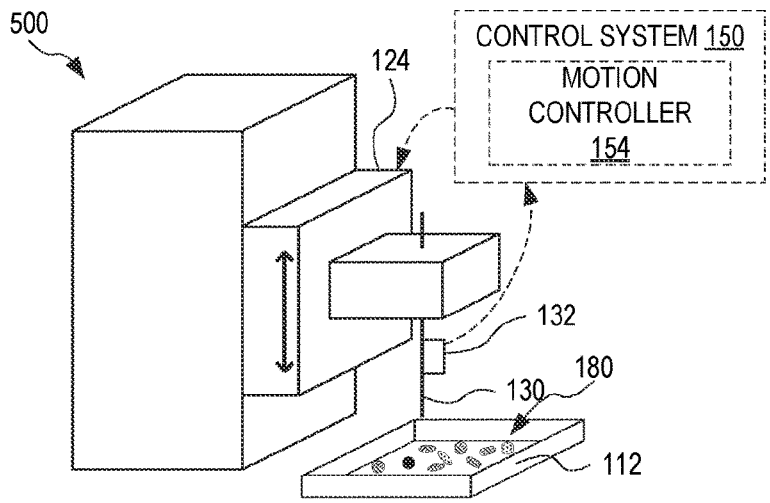
FIG. 5 illustrates a cell extraction module for extracting a pre-selected cell from a sample of cells in cell culture plate, according to an embodiment.

FIG. 5 illustrates one cell extraction module 500 for extracting a pre-selected cell from sample 180 in cell culture plate 112. Cell extraction module 500 includes translation stage 124, needle 130, and sensor 132, configured as discussed above in reference to FIG. 1. Cell extraction module 500 may be implemented in cell sorter 100. Cell extraction module 120 may be communicatively coupled with an embodiment of control system 150 that includes motion controller 154, such that motion controller 154 either allows or prevents downward translation of translation stage 124 according to an output or state of sensor 132.

Figure 6:
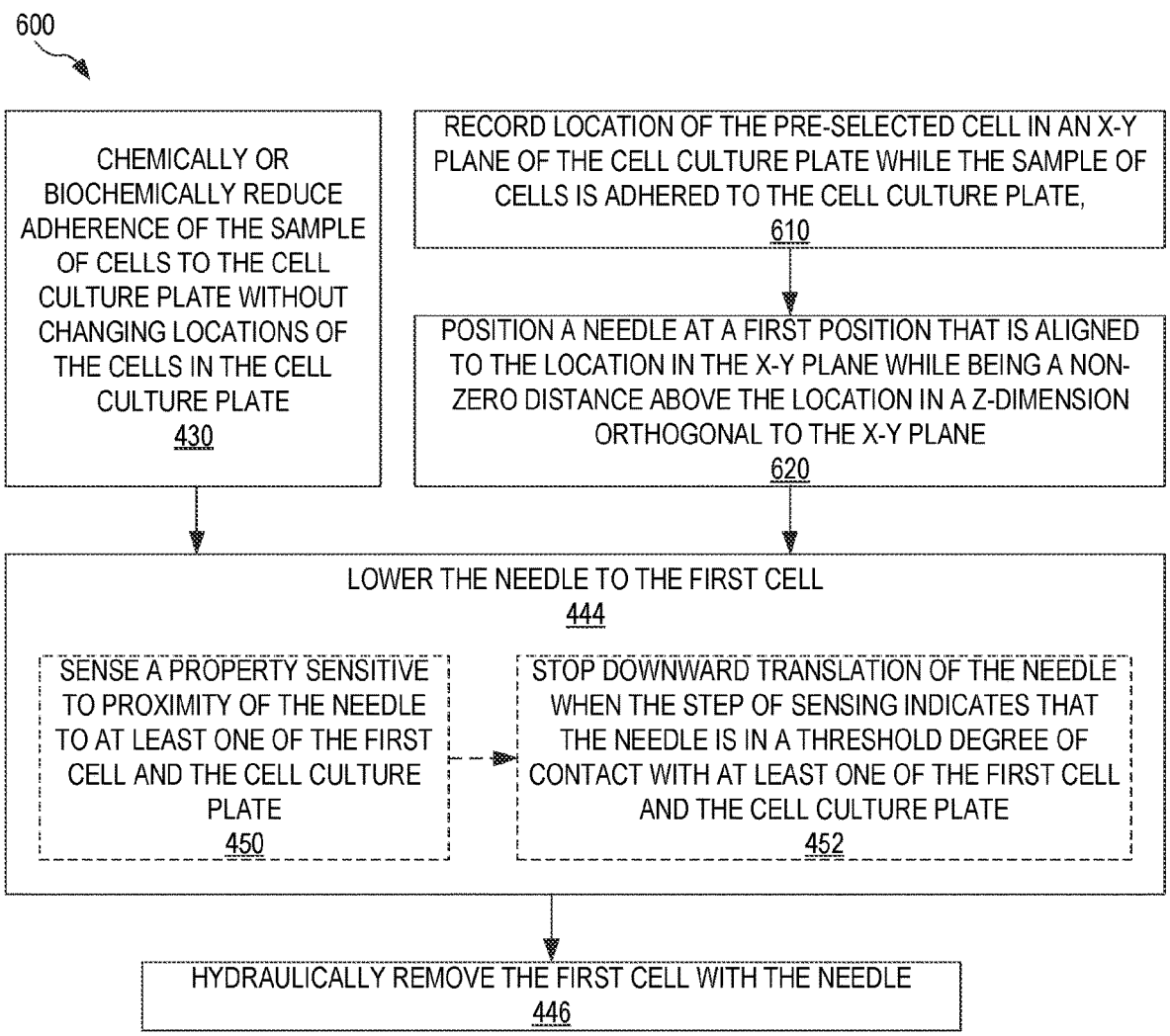
FIG. 6 illustrates a cell extraction method for extracting a pre-selected cell from a sample of cells in a cell culture plate, according to an embodiment.

FIG. 6 illustrates one cell extraction method 600 for extracting a pre-selected cell from a sample of cells in a cell culture plate. Certain embodiments of method 600 may utilize cell extraction module 500 and translation stage 122. Method 600 includes steps 430, 610, 620, 444, and 446. Method 600 may be implemented in method 400.

Step 610 records the location of the pre-selected cell in an x-y plane of the cell culture plate, wherein the recorded location is the location of the pre-selected cell while the cells are adhered to the cell culture plate. In one example of step 610, image analysis module 152 records the location of the selected cell, in the x-y plane, from fluorescence image(s) 182 captured by fluorescence imager 140 while the cells are adhered to cell culture plate 112.

Step 620 positions a needle at a first position, relative to the cell culture plate, that is that is aligned to the location (recorded in step 610) in the x-y plane while being a non-zero distance above this location in the z-dimension. Step 620 is an example of step 442, such that the needle of step 620 is the needle of step 442.

In method 600, (a) step 430 may be performed any time after capture of the fluorescence image(s) from which the location is recorded in step 610, (b) steps 430, 610, and 620 are performed before step 444, and (c) step 446 is performed after step 444. In method 600, step 444 may include steps 450 and 452, for example based on sensor 132 of cell extraction module 500.

Figure 7A:
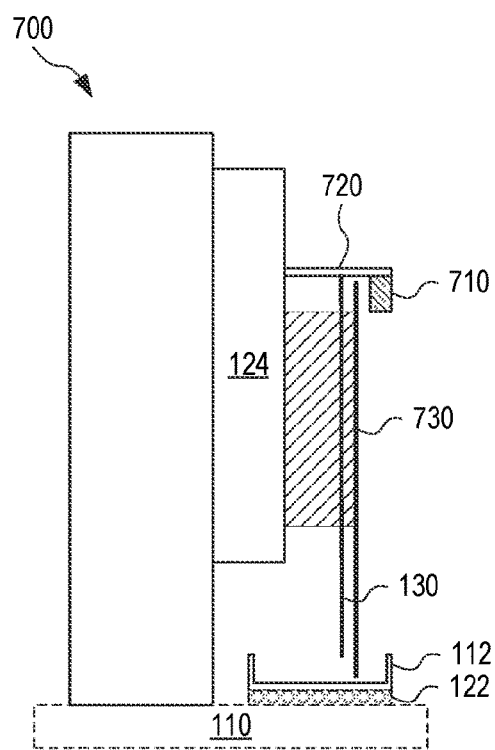
FIGS. 7A and 7B illustrate a cell extraction module that implements a pressure-based mechanism to position a needle, according to an embodiment.
Figure 7B:
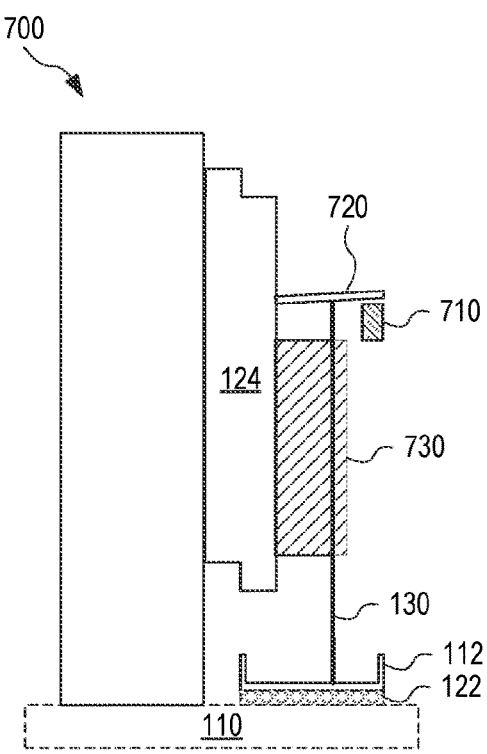

FIGS. 7A and 7B illustrate one cell extraction module 700, an embodiment of cell extraction module 500, that implements a pressure-based mechanism to position needle 130. FIG. 7A shows the state of cell extraction module 700 when needle 130 is a non-zero distance above cell culture plate 112. FIG. 7B shows the state of cell extraction module 700 when needle 130 has been pushed against the bottom of cell culture plate 112. FIGS. 7A and 7B are best viewed together in the following description.

Cell extraction module 700 includes a conductivity sensor 710, a lever 720, and a low-friction mount 730. Conductivity sensor 710 and lever 720 cooperate to form a mechanically activated electrical switch. Conductivity sensor 710 is an embodiment of sensor 132. Low-friction mount 730 mounts needle 130 to translation stage 124 with low friction.

From the starting position shown in FIG. 7A, translation stage 124 lowers low-friction mount 730, needle 130, lever 720, and conductivity sensor 710 together. Until needle 130 reaches cell culture plate 112, the positions of low-friction mount 730, needle 130, lever 720, and conductivity sensor 710, relative to each other, do not change. However, when needle 130 reaches the bottom of cell culture plate 112 (potentially with a portion of sample 180 pressed therebetween), continued downward translation of translation stage 124 causes needle 130 to slide in low-friction amount 730 and push against lever 720 to lift lever 720 away from conductivity sensor 710 (see FIG. 7B). Conductivity sensor 710 detects the loss of electrical contact to lever 720. Control system 150 may be configured to prevent downward translation of translation stage 124 when conductivity sensor 710 indicates that there is no electrical contact to lever 720. Once translation stage 124 travels back up, lever 720 presses needle 130 back down in low-friction mount 730 until lever 720 again rests on conductivity sensor 710. At this point, conductivity sensor 710 detects the electrical contact to lever 720 and control system 150 may once again allow downward translation of translation stage 124.

Figure 8:
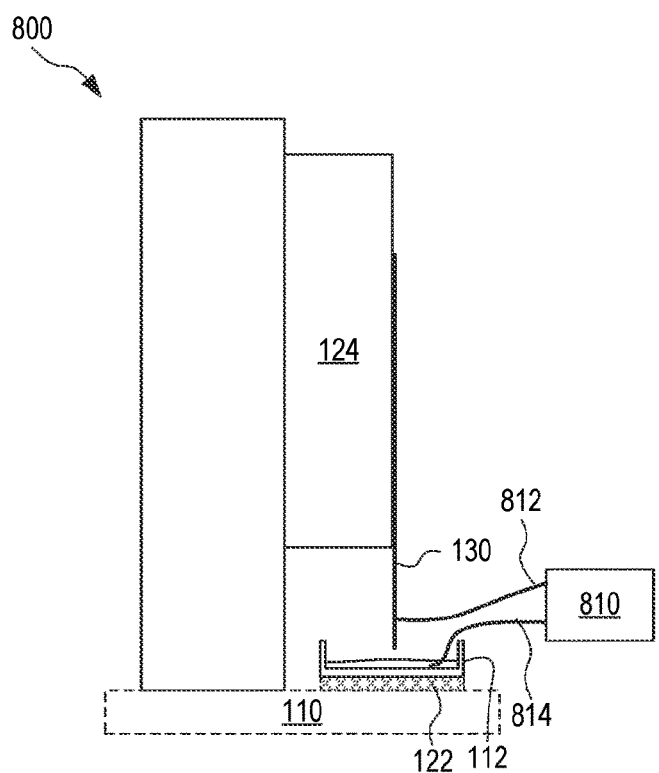
FIG. 8 illustrates a cell extraction module that implements an electrical sensor to position a needle, according to an embodiment.

FIG. 8 illustrates one cell extraction module 800, an embodiment of cell extraction module 500, that implements an electrical sensor 810 to position needle 130. Electrical sensor 810 is coupled between needle 130 (via electrical lead 812) and at least one of sample 180 and cell culture plate 112 (via electrical lead 814). Electrical sensor 810 thus senses whether or not needle 130 is in contact with sample 180. Control system 150 may be configured to prevent downward translation of translation stage 124 when electrical sensor 810 indicates low resistance between needle 130 and sample 180 or cell culture plate 112, and allow downward translation of translation stage 124 only when electrical sensor 810 indicates high resistance between needle 130 and sample 180 or cell culture plate 112.

Changes may be made in the above systems and methods without departing from the scope hereof. It should thus be noted that the matter contained in the above description and shown in the accompanying drawings should be interpreted as illustrative and not in a limiting sense. The following claims are intended to cover generic and specific features described herein, as well as all statements of the scope of the present systems and methods, which, as a matter of language, might be said to fall therebetween.

What is claimed is:

1. A cell sorter comprising:
 a base configured to hold a cell culture plate containing a fluorescently labeled sample of cells;
 a fluorescence imager configured to view the cell culture plate, through bottom of the cell culture plate, to capture one or more fluorescence images of the fluorescently labeled sample of cells; and
 a cell extraction module configured to extract, from above the cell culture plate, a first cell selected from the sample of cells based on the one or more fluorescence images, the cell extraction module including:
  a needle configured to hydraulically remove the first cell from the cell culture plate;
  a first motorized translation stage, coupled to the needle via a low-friction mount, that translates the needle in a z-dimension to reach the first cell from above;
  a second motorized translation stage that translates one of the needle and the cell culture plate in x- and y-dimensions, relative to the other one of the needle and the cell culture plate, to position the needle over the first cell; and
  a sensor, coupled to the needle, and configured to be communicatively coupled to the first motorized translation stage to stop downward translation of the needle, by the first motorized translation stage, when the needle, according to the sensor, is (a) in a threshold degree of contact with at least one of the first cell and the cell culture plate or (b) at a threshold distance above at least one of the first cell and the cell culture plate, the sensor being a mechanically activated electrical switch positioned above the needle such that, when an upward pressure on the needle exceeds friction of the low-friction mount during downward translation by the first motorized translation stage, the needle slides upwards relative to the first motorized translation stage and switches the electrical switch, which causes the downward translation to stop.

2. The cell sorter of claim 1, further comprising a control system configured to control (a) the second motorized translation stage according to the one or more fluorescence images, and (b) the first motorized translation stage according, at least in part, to a state of the electrical switch.

3. The cell sorter of claim 2, the control system including:
a processor; and
non-transitory memory encoding machine-readable instructions that, when executed by the processor, command the processor to effect said control of the first and second motorized translation stages.

4. The cell sorter of claim 3, the machine-readable instructions being configured to allow and stop downward translation by the first motorized translation stage according to a state of the electrical switch.

5. The cell sorter of claim 1, the cell extraction module further including a pump hydraulically coupled with the needle.

6. The cell sorter of claim 1, the cell extraction module further including a charge control module electrically coupled to the needle and configured to apply a transient negative charge to the needle.

7. The cell sorter of claim 1, the second motorized translation stage being incorporated in the base and configured to translate the cell culture plate.

8. A cell extraction module for extracting a pre-selected cell from a sample of cells in a cell culture plate, comprising:
a needle configured to hydraulically remove the pre-selected cell from the cell culture plate;
a motorized translation stage mechanically coupled with the needle via a low-friction mount and configured to translate the needle, in a dimension orthogonal to the cell culture plate, to reach the pre-selected cell from above; and
a sensor, coupled to the needle, and configured to be communicatively coupled to the motorized translation stage to stop downward translation of the needle, by the motorized translation stage, when the needle, according to the sensor, is one of (a) in a threshold degree of contact with at least one of the pre-selected cell and the cell culture plate and (b) at a threshold distance above at least one of the pre-selected cell and the cell culture plate, the sensor being a mechanically activated electrical switch positioned above the needle such that, when an upward pressure on the needle exceeds friction of the low-friction mount during downward translation by the motorized translation stage, the needle slides upwards relative to the first motorized translation stage and switches the electrical switch, which causes the downward translation to stop.

9. The cell extraction module of claim 8, further comprising a control module configured to control the motorized translation stage, the sensor being communicatively coupled to the motorized translation stage via the control module.

10. The cell extraction module of claim 9, the control module including:
a processor; and
non-transitory memory encoding machine-readable instructions that, when executed by the processor, command the processor to effect said control of the motorized translation stage.

11. The cell extraction module of claim 10, the machine-readable instructions being configured to allow and prevent downward translation by the motorized translation stage according to a state of the electrical switch.

12. The cell sorter of claim 1, each of a proximal end and a distal end of the needle being directly above the cell culture plate.

13. The cell sorter of claim 1, wherein the second translation stage translates the needle.

* * * * *